(12) United States Patent
Potts et al.

(10) Patent No.: US 10,085,726 B2
(45) Date of Patent: Oct. 2, 2018

(54) CONTROLLED TRANSFER BIOLOGICAL SAMPLE COLLECTION DEVICES AND METHODS OF USING SUCH DEVICES

(71) Applicant: GE Healthcare UK Limited, Buckinghamshire (GB)

(72) Inventors: Cheryl Louise Potts, Cardiff (GB); Peter James Tatnell, Cardiff (GB); Geraint Seymour, Cardiff (GB); Alan Stuart Pierce, Cardiff (GB); Michael John Smith, Cardiff (GB); Samantha Jane Ogden, Cardiff (GB); Neil John Williams, Cardiff (GB); Christopher Burrows, Cardiff (GB); Jared William Harris Evans, Cardiff (GB); Ashley Edward Bryant, Cardiff (GB); Sean Robert Sweeney, Cardiff (GB)

(73) Assignee: GE HEALTHCARE UK LIMITED, Little Chalfont (GB)

( * ) Notice: Subject to any disclaimer, the term of this patent is extended or adjusted under 35 U.S.C. 154(b) by 0 days.

(21) Appl. No.: 15/101,113

(22) PCT Filed: Nov. 25, 2014

(86) PCT No.: PCT/EP2014/075566
§ 371 (c)(1),
(2) Date: Jun. 2, 2016

(87) PCT Pub. No.: WO2015/086312
PCT Pub. Date: Jun. 18, 2015

(65) Prior Publication Data
US 2016/0302775 A1     Oct. 20, 2016

(30) Foreign Application Priority Data
Dec. 12, 2013 (GB) .................................. 1322011.6

(51) Int. Cl.
*A61B 5/00* (2006.01)
*A61B 10/00* (2006.01)
(Continued)

(52) U.S. Cl.
CPC ...... *A61B 10/0096* (2013.01); *A61B 10/0045* (2013.01); *B01L 3/508* (2013.01);
(Continued)

(58) Field of Classification Search
CPC ............ A61B 10/0096; A61B 10/0045; A61B 10/0275; A61B 2010/0074; A61B 5/1123; A61B 5/14532; A61B 5/14539
(Continued)

(56) References Cited

U.S. PATENT DOCUMENTS

| 5,308,580 A | * 5/1994 | Clark ..................... B01L 3/502 422/419 |
| 5,756,126 A | 5/1998 | Burgoyne |

(Continued)

FOREIGN PATENT DOCUMENTS

| WO | 95/08761 A1 | 3/1995 |
| WO | 2007/099355 A1 | 9/2007 |
| WO | 2012/163788 A1 | 12/2012 |

OTHER PUBLICATIONS

International Search Report and Written Opinion regarding International Application No. PCT/EP2014/075566, dated Jan. 30, 2015.

*Primary Examiner* — May Abouelela
(74) *Attorney, Agent, or Firm* — Eversheds Sutherland (US) LLP

(57) ABSTRACT

A controlled transfer biological sample material collection device is disclosed which comprises: a body; and a sample collection member for collecting the biological sample material (not shown), the body housing a sample storage medium for generally dry storage of the biological material, (Continued)

the collection member being moveable from an exposed position (shown in FIG. 8) where collection of a biological sample is possible, to a transfer position (shown in FIG. 9) which effects transfer of at least a portion of the collected sample to said medium. The device is characterized in that the body slideably supports the sample collection member, and in that the body or collection member include a ramp-like projection portion (116 FIG. 10) operable to force the collection member into the transfer position against the medium and to effect said transfer as the collection member slides within the body.

9 Claims, 10 Drawing Sheets

(51) Int. Cl.
  *B65D 81/00*  (2006.01)
  *B01L 3/00*  (2006.01)
  *C12Q 1/24*  (2006.01)
  *G01N 1/30*  (2006.01)

(52) U.S. Cl.
  CPC .............. *C12Q 1/24* (2013.01); *G01N 1/30* (2013.01); *B01L 2200/141* (2013.01); *B01L 2300/0809* (2013.01)

(58) Field of Classification Search
  USPC .................................................. 600/573, 583
  See application file for complete search history.

(56) References Cited

U.S. PATENT DOCUMENTS

| | | | |
|---|---|---|---|
| 5,939,259 A | 8/1999 | Harvey et al. | |
| 5,972,386 A | 10/1999 | Burgoyne | |
| 5,976,572 A | 11/1999 | Burgoyne | |
| 6,168,922 B1 | 1/2001 | Harvey et al. | |
| 6,294,203 B1 | 9/2001 | Burgoyne | |
| 6,372,516 B1 | 4/2002 | Sun | |
| 6,447,804 B1 | 9/2002 | Burgoyne | |
| 6,627,226 B2 | 9/2003 | Burgoyne et al. | |
| 6,875,185 B2 * | 4/2005 | Wong | A61B 5/145 422/412 |
| 7,294,502 B2 * | 11/2007 | Eckermann | A61B 10/0045 422/537 |
| 7,300,627 B1 * | 11/2007 | Sun | A61B 10/0045 422/417 |
| 7,393,697 B2 * | 7/2008 | Charlton | G01N 33/558 422/412 |
| 7,927,548 B2 * | 4/2011 | Slowey | A61B 10/0051 422/422 |
| 8,025,849 B2 * | 9/2011 | Baldwin | A61B 10/0051 422/400 |
| 8,025,851 B2 * | 9/2011 | Slowey | A61B 10/0051 422/420 |
| 8,071,394 B2 * | 12/2011 | Wu | G01N 33/558 422/401 |
| D686,340 S * | 7/2013 | Smith | D24/225 |
| 8,871,155 B2 * | 10/2014 | Wu | B01L 3/5023 422/400 |
| 2003/0045814 A1 * | 3/2003 | Sangha | A61B 10/0051 600/573 |
| 2003/0113906 A1 * | 6/2003 | Sangha | A61B 10/0051 435/287.2 |
| 2009/0318829 A1 * | 12/2009 | Hannant | A61B 10/0045 600/562 |
| 2010/0106057 A1 * | 4/2010 | Harvey | B01L 3/5023 600/573 |
| 2014/0100480 A1 * | 4/2014 | Pierce | A61B 10/0045 600/573 |
| 2014/0303518 A1 * | 10/2014 | Pierce | B01L 3/5055 600/573 |

* cited by examiner

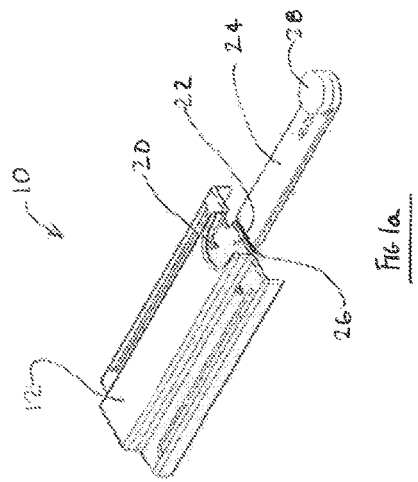
Step 1
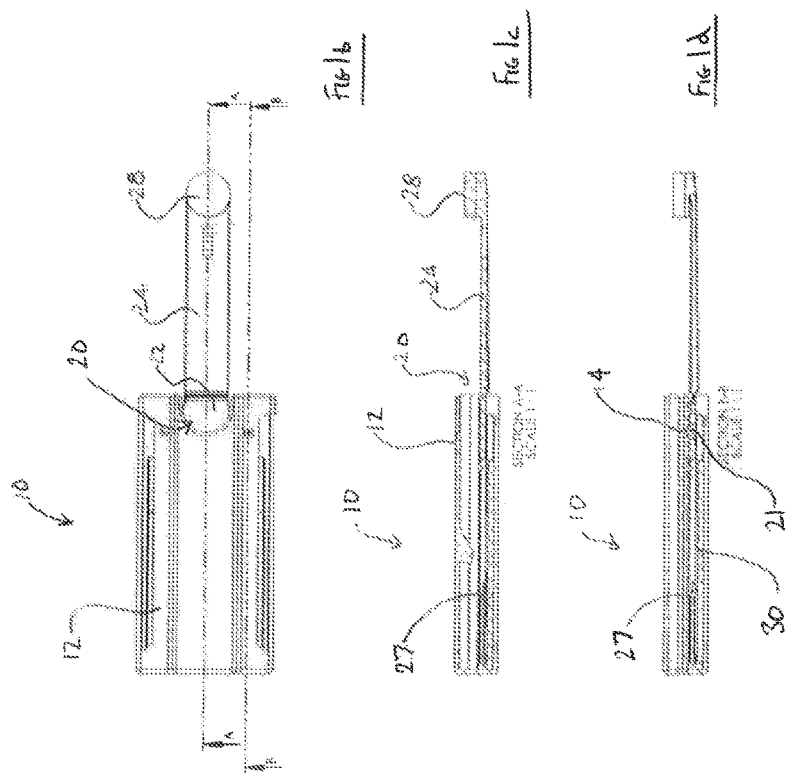

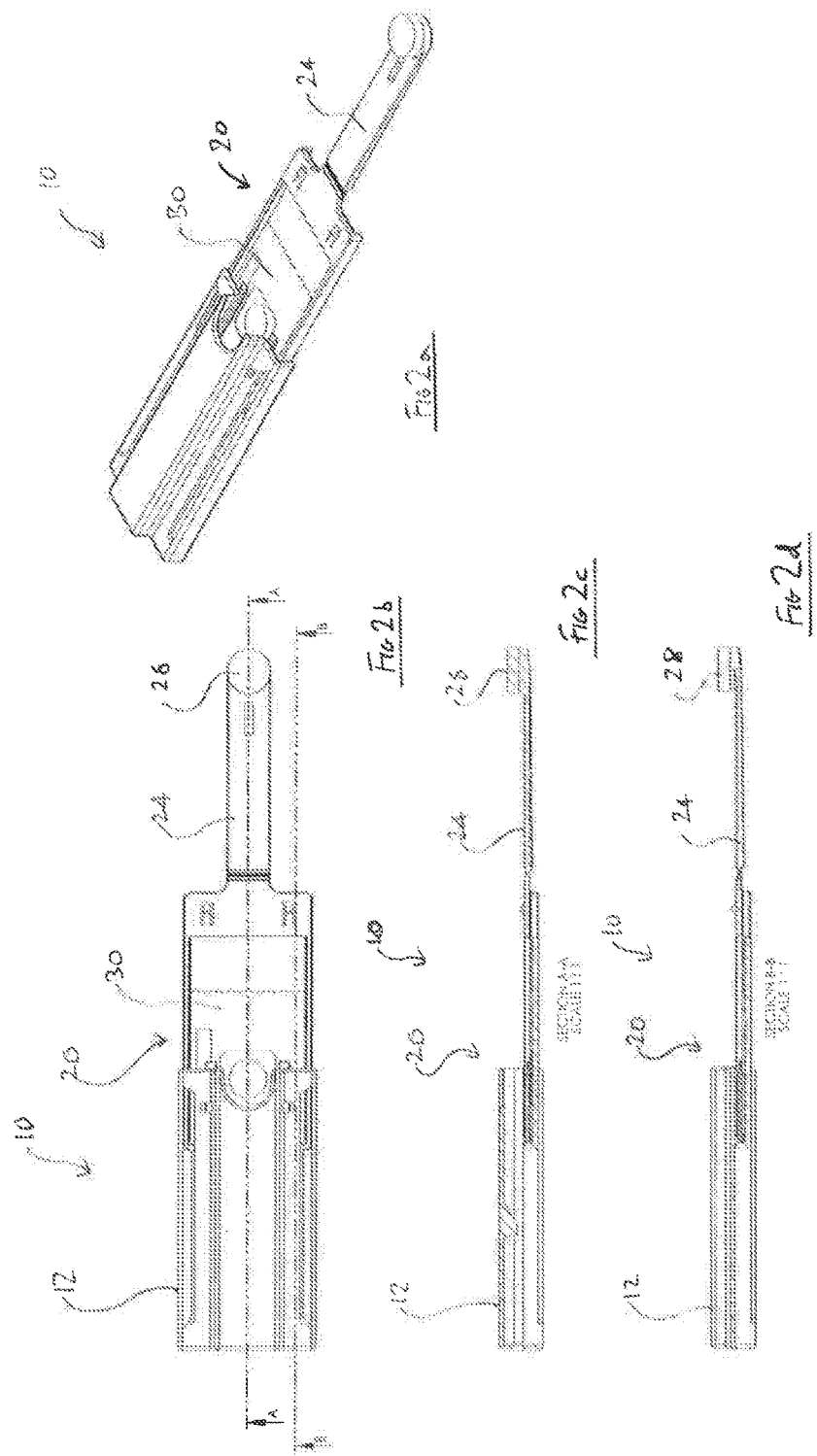

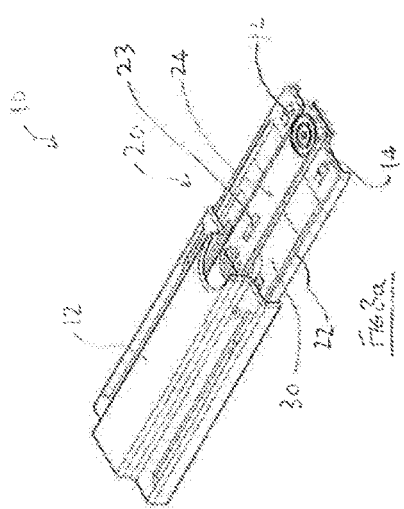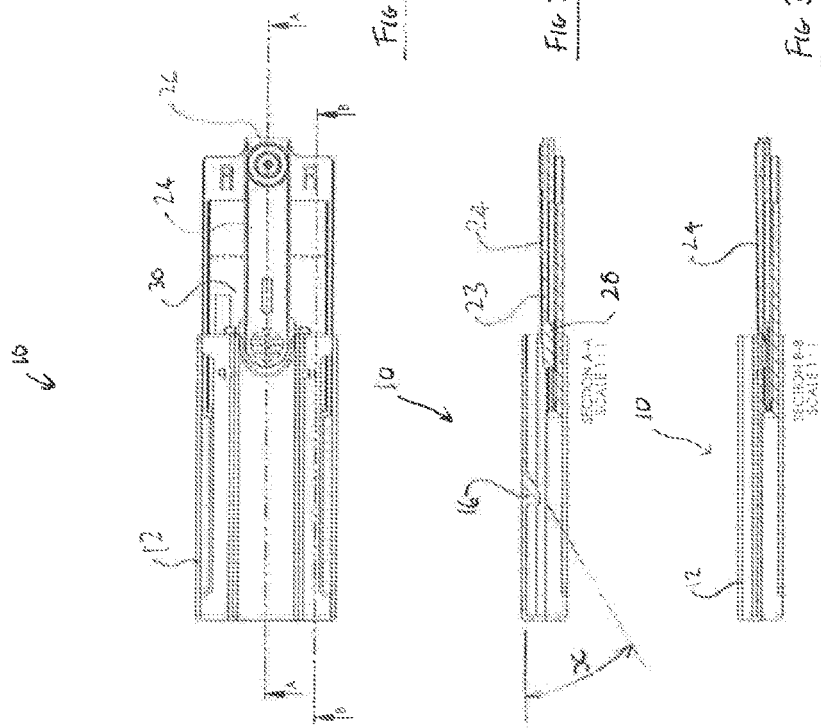

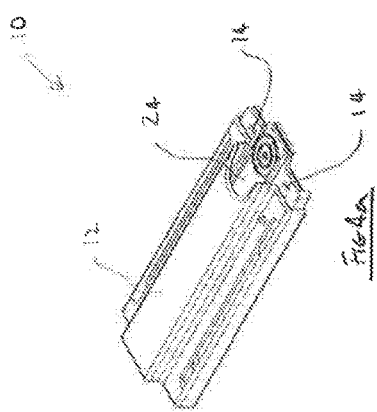
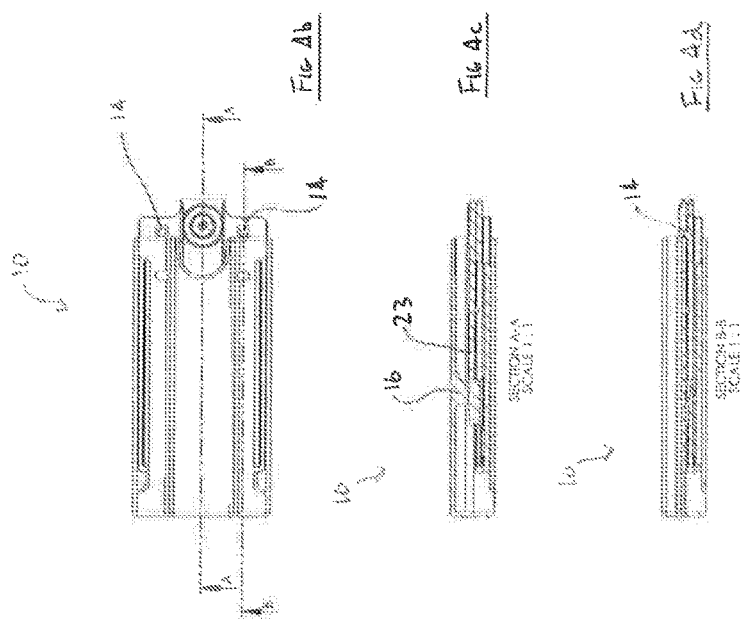
Step 4

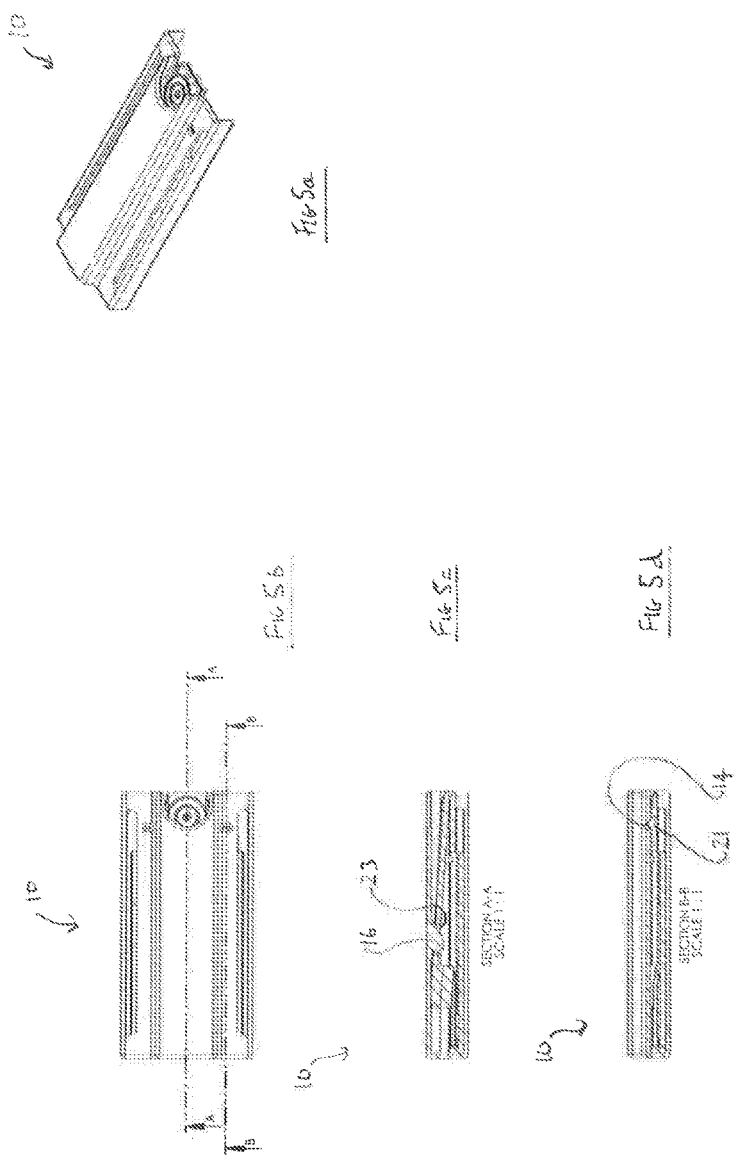

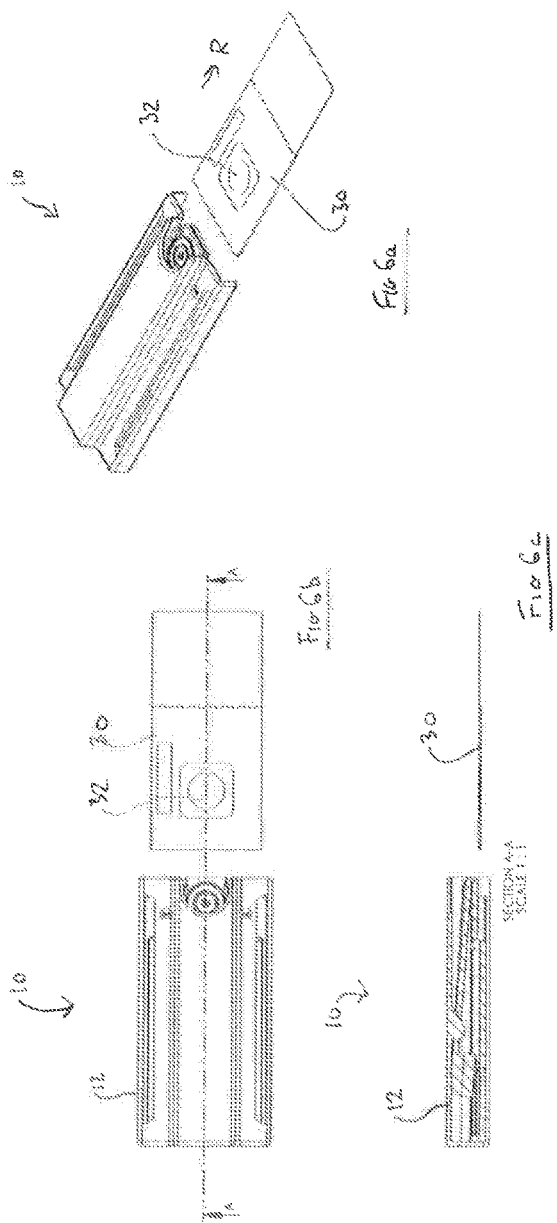

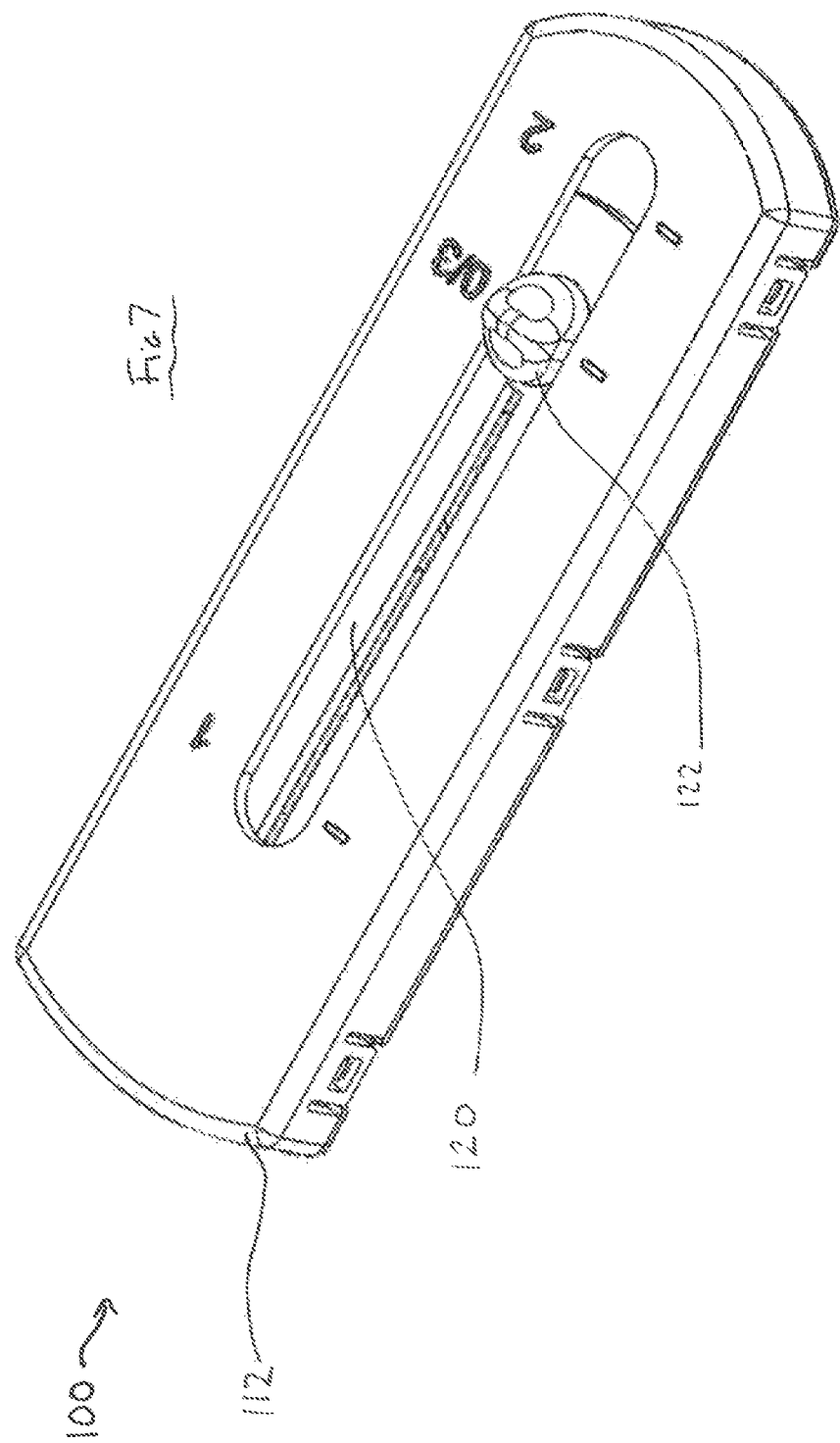

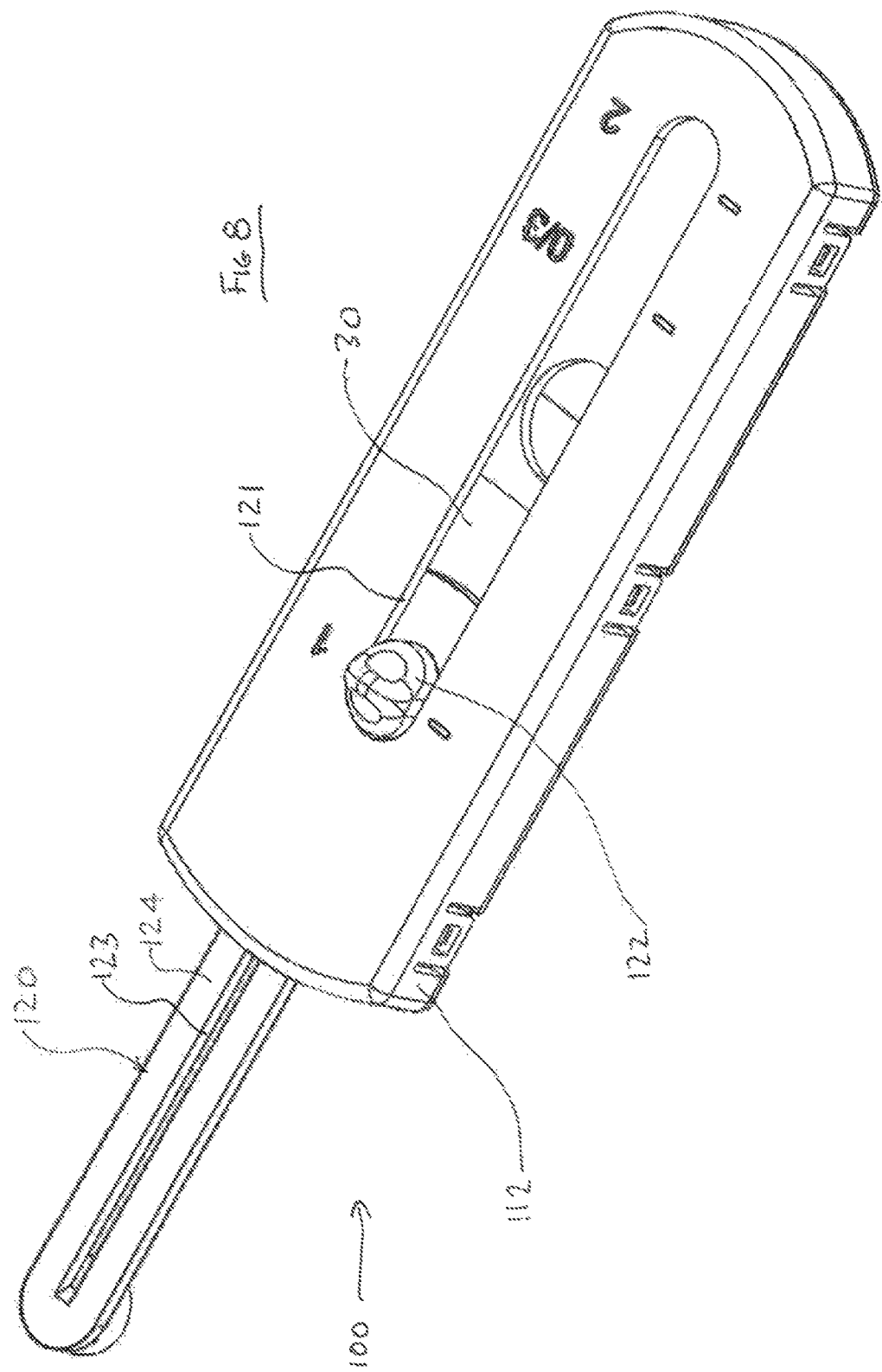

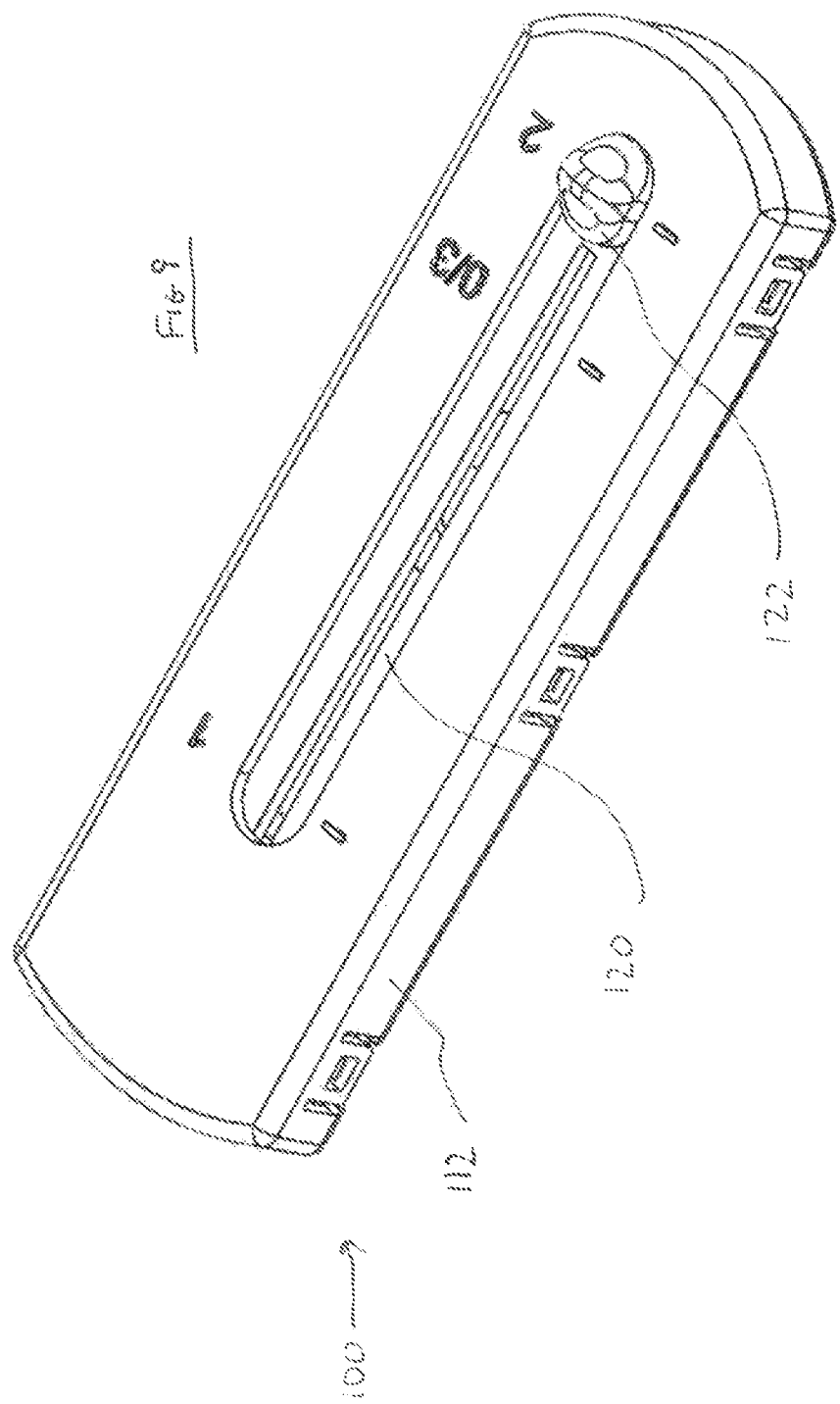

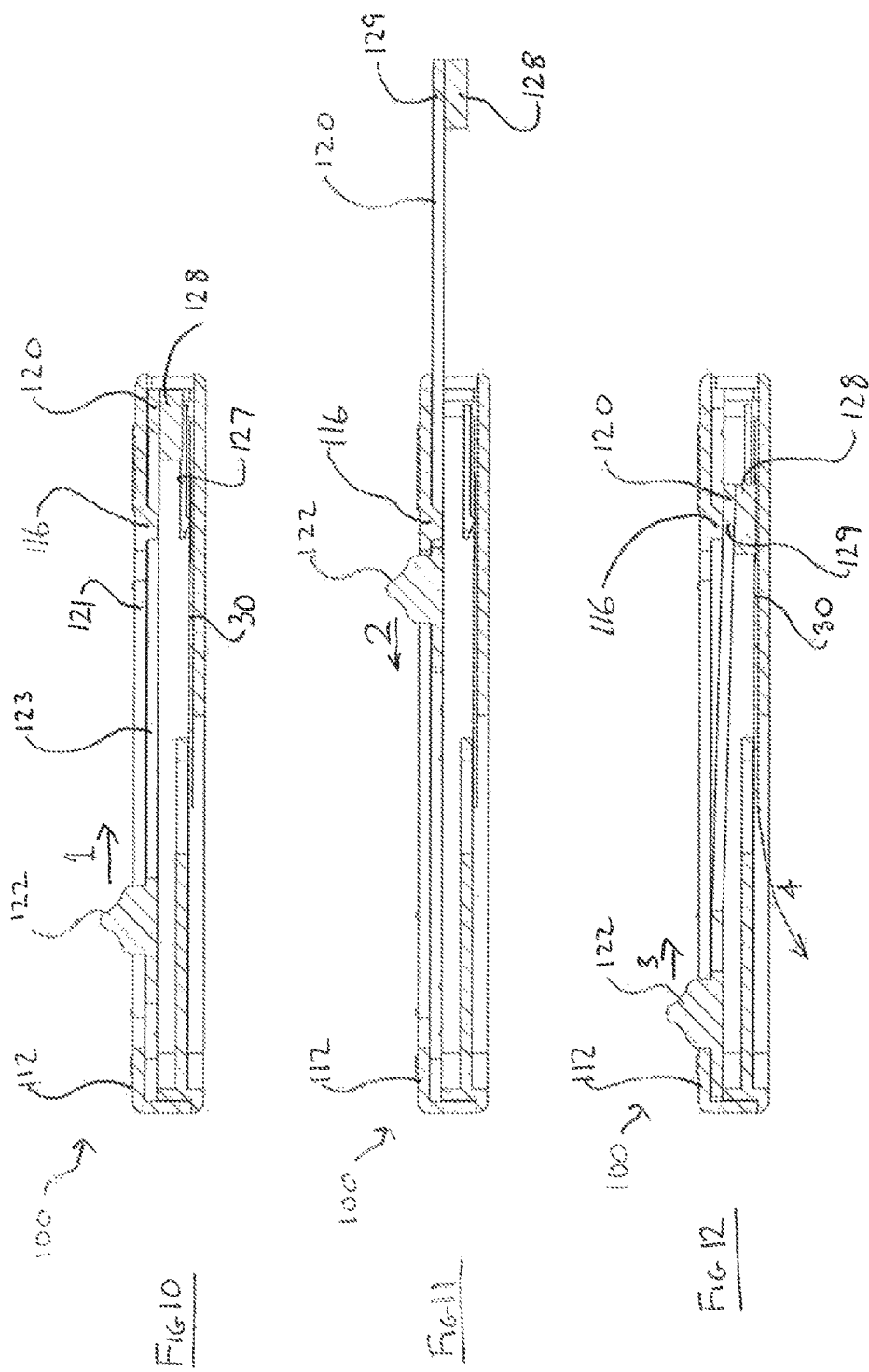

CONTROLLED TRANSFER BIOLOGICAL SAMPLE COLLECTION DEVICES AND METHODS OF USING SUCH DEVICES

CROSS-REFERENCE TO RELATED APPLICATIONS

This application is a filing under 35 U.S.C. 371 of international application number PCT/EP2014/075566, filed Nov. 25, 2014, which claims priority to GB application number 1322011.6, filed Dec. 12, 2013, the entire disclosures of each of which are hereby incorporated by reference.

BACKGROUND OF THE INVENTION

Field of the Invention

The field of the present invention relates to a controlled transfer biological collection device using a dry solid transfer and storage medium, and a method for the collection of biological material of interest, for example genetic or proteinaceous material, in a form suitable for temporary or long term storage, and/or subsequent analysis. Specifically, the present invention provides for a sampling device that controls the transfer of the biological sample to the storage medium by holding the storage medium and a moveable sample collection member having an analyte collection surface.

Description of the Related Art

The collection of biological samples (such as blood) and extracting DNA for genetic analysis from the sample has been widely used by the forensics and medical community for identification purposes, for paternity testing, for genetic diagnostic testing in new born screening programs, for genetic typing for predisposition to disease and for genetic characterisation for drug susceptibility. However, due to the invasive nature of blood collection, alternative non-invasive methods are coming into favour. Current methods involve scraping cellular mucosa from inside the oral cavity using any of a number of different devices such as cytobrushes, cotton or artificial fibre swabs, mouthwash swish and rinse methods, foam tipped swabs, and supported cellulosic filter paper collection techniques (known as the Bode method). These methods require time-consuming, labour intensive extraction methods.

The introduction of treated storage media into the forensics community has significantly streamlined the collection and extraction of DNA from a variety of samples. One such treated medium is available commercially under the brand name FTA® from Whatman, Inc. and is described in one or more of the following patents U.S. Pat. No. 6,627,226, U.S. Pat. No. 6,447,804, U.S. Pat. No. 6,294,203, U.S. Pat. No. 6,168,922, U.S. Pat. No. 5,976,572, U.S. Pat. No. 5,972,386, U.S. Pat. No. 5,939,259, and U.S. Pat. No. 5,756,126. The medium is used with a plastics collecting device known as Easicollect® from Whatman Inc, and described in US20100106057 (Harvey et al). This known collecting device includes an arm having buccal cell collector foam pad at one end, which arm is manipulated to collect buccal cells, and is further manipulated to pivot, and thereby to transfer those cells from the foam pad onto an FTA medium held at an opposing end of the device.

Whilst this technique is adequate, the transfer buccal cells to the treated medium in a consistent and reproducible manner remains a matter of operator skill, which is not ideal particularly where operators may seldom use the device. The correct pressure and timing of the transfer step are important, and it is essential that the exposed medium is not contaminated while transfer takes place.

Improvements in the device design were disclosed in WO2012/163788 (GE Healthcare), however, the inventors have realised that yet further improvements in the ease of use and prevention of contamination are possible.

BRIEF SUMMARY OF THE INVENTION

The present invention relates to a controlled transfer biological collection device using a dry solid storage and transfer medium and a method for the collection of biological material of interest—a sample (which may be genetic or proteinaceous material) in a form suitable for storage and/or subsequent analysis.

According to a first aspect, the invention provides a controlled transfer biological sample material collection device, comprising: a body; and a sample collection member for collecting the biological sample material, the body housing a sample storage medium for generally dry storage of the biological material, the collection member being moveable from an exposed position where collection of a biological sample is possible, to a transfer position which effects transfer of at least a portion of the collected sample to said medium, the device being characterised in that the body slideably supports the sample collection member, and in that the body or collection member include a projection operable to force the collection member into the transfer position against the medium and to effect said transfer as the collection member slides within the body.

In an embodiment, said projection is a ramp-like projection.

In an embodiment, the collection member includes a slot and the projection is accommodated within the slot until the collection member is in the transfer position, whereat the projection abuts the collection member and causes said forcing.

In an embodiment, said movement is sliding movement effected by manual operation of a button projecting from the body.

In an embodiment, the collection member includes a portion slideable within the body which slideable portion carries the medium.

In an embodiment, the collection member further includes an arm hinged to the slideable portion, which arm carries a resilient pad for sample collection, wherein the slideable portion and the arm are foldable together to provide a folded together position, to slide within the body to effect the transfer under the influence of the projection.

In an embodiment, the projection is formed on the body, and the arm includes a release slot, which slot accepts the projection thereby to separate the medium and the pad following the transfer.

In an embodiment, the slideable portion and medium are positionable within the body so as to be substantially enclosed by the body, and when in that position, the arm is able to adopt said exposed position, and the slideable portion and medium are further positionable so as to be only partially within the body but able to adopt said folded together position with the arm, for collective reinsertion into the body and to effect said transfer.

In an embodiment, the extent of movement of the collection member is limited by complementary stop features on the body and on the member.

In an embodiment, the medium is removable from the slideable portion.

According to a second aspect, the invention provides a method for controlled transfer biological sample material collection, the method including the steps of: i) providing a device, comprising: a body and a sample collection member for collecting the biological sample material, the body housing a sample storage medium for generally dry storage of the biological material, ii) exposing the collection member and collecting a biological sample on the collection member; iii) moving the collection member from an exposed position where collection of a biological sample is possible, to a transfer position which effects transfer of at least a portion of the collected sample to said medium, iv) providing a projection on the body or on the collection member, and sliding the collection member relative to the body to said transfer position, whereat the projection forces the collection member against the medium.

The invention extends to using the device according to the first or second aspect wherein the medium is substantially enclosed by the housing, to avoid contamination of the sample storage medium.

The invention can be put into effect in numerous ways, typical embodiments of which are described below with reference to the drawings, wherein:

BRIEF DESCRIPTION OF THE DRAWINGS

FIG. 1a is a perspective view of an embodiment of a collection device in an initial position;

FIG. 1b is a plan view of the device shown in FIG. 1;

FIGS. 1c and 1d are sections through the device shown in FIG. 1b;

FIG. 2a through to FIG. 6c are further views of the device of FIG. 1a, in different positions;

FIG. 7 is perspective view of another embodiment of a collection device in an initial position;

FIG. 8 is a perspective view of the device shown in FIG. 7 but in a sample collection position;

FIG. 9 is a perspective view of the device shown in FIG. 7 but in a sample transfer position; and FIGS. 10, 11 and 12 are sectional views of the device shown in FIGS. 7, 8 and 9 respectively.

DETAILED DESCRIPTION OF THE INVENTION

An embodiment of the invention is shown in FIG. 1a. A collection device 10 for a biological sample that contains degradable biologically sourced analytes is shown which comprises a body 12 which slideably houses a collection member 20. The collection member has a sample storage portion in the form of a tray 22 for supporting a sample storage medium 30. Examples of a storage medium material a suitable for the present invention include untreated filter paper, such as #903® brand paper (Whatman, Inc., Florham Park, N.J. USA) or treated filter papers, such as FTA and FTA Elute brand paper (also from Whatman, Inc., Florham Park, N.J. USA). These treated media are described in US patents referenced above. Such treated media provide a simple safe method for collection, shipping and storage of biological samples. They also contain chemistries which make it easy to isolate nucleic acids from complex samples such as blood. Samples collected on treated or untreated media are dried for storage and can be stored at room temperature for long periods of time.

The collection member 20 further includes an arm 24 hinged to the sample storage portion by means of a hinge 26 formed from flexible moulded plastics. At the distal end of arm 24 a resilient pad 28 of foamed polymeric material is fixed to the arm, which acts as a sample collector when required.

In the position shown in FIGS. 1a and 1b, the device is ready to be used to collect a biological sample by wiping the pad 28, or otherwise making contact, over an area of interest, for example to collect buccal cells from the inner cheek surface of the mouth of a subject.

FIG. 1b shows the device 10 in plan view. FIG. 1c shows the device 10 in section along line A-A in FIG. 1b, and FIG. 1d shows the device in section along line B-B. As can be seen in more detail in FIGS. 1c and 1d, the tray 22 holds a storage medium 30, and the tray 22 is slideable in the body 12 along with the medium 30 and the arm 24. However, the tray is held resiliently in position by means of detents 21 formed on the tray 22 which cooperate with apertures 14 in the body 12.

Once the sample has been collected, the collection member 20 is drawn out of the body 12 as shown in FIG. 2a, until the tray abuts further stop members. Further details are shown in FIGS. 2b, 2c and 2d. In that position, the medium 30 becomes exposed.

The arm 24 is then folded over toward the medium 30 as illustrated in FIGS. 3a, 3b, 3c and 3d. In this position, the pad 28 may lightly touch the medium 30 to transfer some biological sample material to the medium but that is not certain. It will be noted that the arm 24 includes a release through-slot 23, the function of which is described in more detail below.

The user then pushes the collection member 30 back into the body 12 holding the arm folded, as shown in FIG. 4a. The user will feel resistance as the detents 14 abut the edge of the body 12. At this point a ramp 16 on the body 12 forces the back of the arm 24, adjacent the pad 28, toward the medium 28 to provide a repeatable and constant contact force, and thereby a controlled transfer of biological material onto the medium 30 is obtained.

The user pauses with the device 10 in this position for a predetermined time. It has been found that force is a more accurate predictor of material transference rather than time so the pause time is not critical, but 5 to 15 seconds has proven successful, more preferably about 10 seconds.

The user then pushes the tray 22 fully into the body 12, until the pad lifts off the medium 30. This lifting occurs when the through slot 23 coincides with the ramp 16 so the through slot surrounds the ramp 16. This position is shown in FIGS. 5a, 5b, 5c, and 5d. In this position the complementary features 14 and 21 once again come into alignment. The user can then either remove the medium 30 as shown in FIGS. 6a, 6b and 6c, for storage, or transportation to a laboratory for storage or further processing, or may do the same with the whole device still containing the medium 30.

Since the medium may contain at least one stabilizing reagent the sample will then be preserved for transport or storage. Suitable such reagents include either the combination of a weak base, a chelating agent, and, optionally, uric acid or a urate salt or simply the addition of a chaotropic salt, alone or in combination with a surfactant. The "weak base" of the composition may be a Lewis base which has a pH of about 6 to 10, preferably about pH 8 to 9.5. One function of the weak base is to act as a buffer to maintain a composition pH of about 6 to 10, preferably about pH 8.0 to 9.5, for example, pH 8.6. Hence, a weak base suitable for the composition of the invention may, in conjunction with other components of the composition, provide a composition pH of 6 to 10, preferably, about pH 8.0 to 9.5. Suitable weak bases according to the invention include organic and inorganic bases. Suitable inorganic weak bases include, for example, an alkali metal carbonate, bicarbonate, phosphate or borate (e.g., sodium, lithium, or potassium carbonate). Suitable organic weak bases include, for example, tris-hydroxymethyl amino methane (Tris), ethanolamine, tri-ethanolamine and glycine and alkaline salts of organic acids (e.g., trisodium citrate). A preferred organic weak base is a weak monovalent organic base, for example, Tris. The Tris may be either a free base or a salt, for example, a carbonate salt.

A preferred chelating agent is a strong chelating agent. By "strong" chelating agent it is meant that the agent binds multivalent metal ions with a comparable or better affinity than ethylene diamine tetraacetic acid (EDTA). A preferred chelating agent according to the invention is EDTA.

Anioinic surfactants are examples of surfactants which are useful in the present invention. A preferred anionic detergent is a strong anionic detergent. As used herein, a "strong" anionic detergent includes a hydrocarbon moiety, aliphatic or aromatic, containing one or more anionic groups. Particularly preferred anionic detergents suitable for the invention include sodium dodecyl sulphate (SDS) and sodium lauryl sarcosinate (SLS). In a preferred embodiment, the anionic detergent causes inactivation of most microorganisms which have protein or lipids in their outer membranes or capsids, for example, fungi, bacteria or viruses. This includes microorganisms which may be pathogenic to humans and are present in a biological sample. Also preferably, the storage medium will have a visual delineation (32 FIG. 6a) placed around the transfer area of the storage medium such that if removed from the tray 22 a user will know where the material was deposited without reference to the device.

Where a chaotropic salt only is applied to the medium than it is preferred that this slat is guanidinium thiocyanate.

The present device 10 can be used to collect samples such as degradable biologically sourced analytes such as nucleic acids, proteins, and respective fragments thereof. The biological sample can be selected from the group consisting of saliva, blood, serum, lymph fluids, buccal cells, mucosal cells, cerebrospinal fluid, semen, vaginal fluid, faeces, plasma, urine, a suspension of cells, or a suspension of cells and viruses.

Preferably, the present device is dimensioned and configured such that tray 22 releasably holds the storage medium 30 by holding means 27 in the form of resilient tabs. Thus, one can separate the medium 30 from the remainder of the device 10 for subsequent processing or storage. The tension on the tabs 27 allows for manual or automated extraction, but does not allow for accidental loss of the medium 30.

FIGS. 7 to 10 show a further embodiment of the invention which is similar in size and function to the embodiment described above and is intended to hold the same storage medium (30 FIG. 10). A sample collector 100 is shown, which has a body 112 and a collection member 120 slideable generally within the body and being slideable by means of an associated thumb button 122 projecting from the body.

In FIG. 7 the button 122 is positioned such that the collection member 120 is in the stored position—position 0. In FIG. 8 the button is positioned such that the collection member is deployed in a sample collecting position—position 1, and in FIG. 9 the button has been moved to a sample transfer position—position 2. In operation the button is finally moved from position 2 back to position 3 which is the same as position 0, for transport, if required.

FIG. 10 shows a mid-section of the device 100, in the position shown in FIG. 1. In this position the plastics moulded collection member 120 is visible in section within the body and it can be seen that the member includes, at a proximal end, the slider button 122, an enlongate collection arm 124, formed with a longitudinal slot 123 (also shown in FIG. 8), and at a distal end, sample collection pad 128. The sample storage medium 30 is housed also with the body, and like the first embodiment, is held resiliently in place by a resilient tab 127.

In operation the button 122 is pushed by the user in the direction of arrow 1 in FIG. 10 to position 1 shown in FIG. 8. FIG. 11 shows a mid-sectional view of the device when deployed in position 1. In this position, the arm 124 is exposed outside of the body 112 such that the collection pad 128 is able to collect a biological sample as described above. The collection member 120 is prevented from extending beyond position 1 because the button 122 abuts the end of its aperture 121, thereby providing a stop feature.

Once a sample is collected on the pad 128, the button is moved by the user in the direction of arrow 2 to position 2 shown in FIG. 9. FIG. 12 shows a mid-sectional view of the device when in position 2. In this position, a ramped projection 116 extending from the body 112 abuts the termination 129 of the slot 123, and together with the movement caused by the operation of the button in the direction of arrow 2, causes the arm 124 and pad 128 to be urged against the medium 30 in the body. This urging transfers biological material onto the medium 30 in a controlled way. Further movement of the button in the direction of arrow 3 returns the arm 124 to the starting position 0/3. The medium 30 can be removed from the device 120 if required by sliding the same in the direction of arrow 4 in FIG. 12.

It can be seen that the second embodiment functions in a similar way to the first embodiment, except that the first embodiment has a folding arm 24, which is more use for reaching into deeper cavities to recover a biological sample.

If used in buccal cell collection, the pad 28/128 should be dimensioned and configured to fit within the human mouth. For record keeping and traceability the present device should also comprise an identification label (such as conventional bar coding) on not only the medium 30, but also the body 12/112. RFID tags may be employed for this purpose.

To ensure integrity of the devices 10/100, the present devices can also comprise a sterility envelope surrounding the other device elements. Preferably, those other elements are sterile and free from any biological sample analytes (made for example, from medical grade plastics), which can be done through conventional techniques such as irradiation after the envelope is sealed.

Kits can be made that incorporate the above devices 10/100 along with any combination of associated equipment or reagents including purification reagents, buffers, or the like and storage systems, containers, or the like. In this regard, the present invention further provides a kit comprising a device as defined herein and one or more components selected from the group consisting of purification reagents for subsequent analysis of the sample, buffers, storage systems and containers.

Example of the Devices' Use:

The present devices can be used for biological sample collection for the following
purposes: the collection of buccal cell samples for criminal databases; the collection of crime scene samples (i.e., rehydrated blood, semen, saliva and liquid samples of the same); the collection of sexual assault samples; the collection of buccal samples for population genetics or pharmacogenomics studies; the collection of buccal samples for personal genetic ID archiving; the collection of bacterial or parasite samples from food sources; the collection of blood from meat at slaughterhouse for meat traceability; or the collection of biological samples from animals for veterinary diagnostics.

Although two embodiments only have been illustrated, it will be apparent to the skilled addressee that modifications, variants, additions and omissions are possible within the scope and spirit of the invention defined herein.

For example, a ramp 16/116 has been described and illustrated, but any ramp-like projection could be used, i.e. a projection which forms an acute angle between the direction of sliding of the collection member 20/120 and the surface of the ramp or projection. The acute angle is preferably about 30 degrees as illustrated by the angle x in FIG. 3c. The ramp has been shown on the body 12/112, but an equally effective arrangement would be to mount the ramp on the arm 24/124, and have a reaction surface on the body. Sliding the arm beyond the reaction surface could release the arm from the transfer position in the same way that the slot 23 releases the arm. 'Sliding' and similar terms mean linear or substantially linear movement.

Moulded plastics is the preferred material for the body 12/112 and collection member 20/120, but other materials could be employed, for example metals, for example diecast aluminium alloy.

The embodiments shown provide a sample collection device which houses a sample collection medium that is not exposed during sample collection, to reduce the likelihood of cross contamination of the sample collection medium.

The invention claimed is:

1. A controlled transfer biological sample material collection device, comprising:
   a body housing a sample storage medium suitable for dry storage of a biological material; and
   a plastic biological sample collection member having a pad configured for biological sample collection disposed at one end of the biological sample collection member, the biological sample collection member being moveable from an exposed position wherein the pad extends away from the body to a transfer position wherein the pad contacts the sample storage medium,
   wherein the body slideably supports the biological sample collection member,
   wherein the body or the biological sample collection member include a projection arranged to force the biological sample collection member into the transfer position as the biological sample collection member slides within the body,
   wherein a slideable portion of the biological sample collection member carries the sample storage medium,
   wherein the biological sample collection member includes an arm hinged to the slideable portion,
   wherein the arm comprises the pad, and
   wherein the slideable portion and the arm are foldable together to form a folded together position that is slideable within the body and assumes the transfer position under the influence of the projection.

2. The device of claim 1, wherein said projection is a ramp projection.

3. The device of claim 1, wherein the biological sample collection member includes a slot, wherein the body includes the projection, wherein the slot accommodates the projection except in the transfer position, and wherein the projection abuts the biological sample collection member in the transfer position and is configured to force the biological sample collection member into the transfer position.

4. The device of claim 1, further comprising a button projecting from the body that is operable to slide the biological sample collection member between the exposed position and the transfer position.

5. The device of claim 1, wherein the body comprises the projection, wherein the arm includes a release slot, and wherein the release slot is arranged to accept the projection and separate the sample storage medium and the pad.

6. The device of claim 5, wherein the slideable portion and the sample storage medium are positionable within the body to be substantially enclosed by the body, wherein the arm can extend away from the body when the slideable portion and the sample storage medium are positioned within the body, and wherein the slideable portion and the sample storage medium are further positonable so as to be only partially within the body but able to adopt said folded together position with the arm.

7. The device of claim 1, wherein movement of the biological sample collection member is limited by complementary stop features on the body and on the biological sample collection member.

8. The device of claim 1, wherein the sample storage medium is removable from the slideable portion.

9. A method for controlled transfer biological sample material collection, the method including the steps of:
   i) providing a device according to claim 1;
   ii) exposing the pad on the biological sample collection member;
   iii) collecting a biological sample on the pad of the biological sample collection member;
   iv) moving the biological sample collection member from the exposed position to the transfer position to effect transfer of at least a portion of the collected biological sample to said sample storage medium, wherein sliding the biological sample collection member relative to the body causes the projection to force the biological sample collection member into the transfer position.

* * * * *